(12) United States Patent
Butler

(10) Patent No.: US 8,979,905 B2
(45) Date of Patent: Mar. 17, 2015

(54) SPINAL ROD

(75) Inventor: Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 201 days.

(21) Appl. No.: 12/556,898

(22) Filed: Sep. 10, 2009

(65) Prior Publication Data

US 2010/0063544 A1    Mar. 11, 2010

Related U.S. Application Data

(60) Provisional application No. 61/095,650, filed on Sep. 10, 2008.

(51) Int. Cl.
*A61B 17/70*    (2006.01)

(52) U.S. Cl.
CPC .......... *A61B 17/701* (2013.01); *A61B 17/7011* (2013.01); *A61B 17/7032* (2013.01); *A61B 17/7083* (2013.01)
USPC ........................................................ 606/261

(58) Field of Classification Search
USPC .................................. 606/264–278, 61–262
See application file for complete search history.

(56) References Cited

U.S. PATENT DOCUMENTS

| 5,591,235 | A * | 1/1997 | Kuslich ........................... 606/261 |
| 5,651,789 | A | 7/1997 | Cotrel |
| 2001/0055746 | A1 * | 12/2001 | Salvo ............................. 434/203 |
| 2005/0070901 | A1 * | 3/2005 | David ............................. 606/61 |
| 2005/0216000 | A1 * | 9/2005 | Colleran et al. ................. 606/61 |
| 2006/0025768 | A1 * | 2/2006 | Iott et al. ......................... 606/61 |
| 2006/0241594 | A1 * | 10/2006 | McCarthy et al. .............. 606/61 |
| 2007/0093820 | A1 * | 4/2007 | Freudiger ........................ 606/61 |
| 2007/0173825 | A1 * | 7/2007 | Sharifi-Mehr et al. .......... 606/61 |
| 2007/0191841 | A1 * | 8/2007 | Justis et al. ..................... 606/61 |
| 2007/0270819 | A1 * | 11/2007 | Justis et al. ..................... 606/61 |
| 2008/0071276 | A1 * | 3/2008 | Ferree ............................. 606/61 |
| 2008/0177318 | A1 | 7/2008 | Veldman et al. |
| 2008/0294194 | A1 * | 11/2008 | Capote et al. ................. 606/246 |
| 2009/0048632 | A1 * | 2/2009 | Firkins et al. ................. 606/246 |
| 2009/0093820 | A1 * | 4/2009 | Trieu et al. .................... 606/103 |
| 2009/0163955 | A1 * | 6/2009 | Moumene et al. ............ 606/257 |
| 2009/0222042 | A1 * | 9/2009 | Firkins et al. ................. 606/246 |

(Continued)

FOREIGN PATENT DOCUMENTS

FR    2743290 A1    7/1997

*Primary Examiner* — Mary Hoffman
*Assistant Examiner* — Michelle C Eckman
(74) *Attorney, Agent, or Firm* — Foley & Lardner LLP

(57) ABSTRACT

A spine or spinal rod has a cross-section defining angled sides that cooperate with a spinal rod opening of a spinal rod holder. In one form, the spine rod has an essentially pentagonal cross-section that thus essentially defines angled sides or side surfaces that interact with the spinal rod holder opening to positively seat the spine rod into the spinal rod holder and prevent spine rod from rotation. In the pentagonal cross-section form, the spine rod has a top or posterior side/side surface, a bottom or anterior side/side surface, a first lateral side/side surface, a second lateral side/side surface, a first angled sub-lateral side/side surface and a second angled sub-lateral side/side surface. The first and second angled sub-lateral sides/side surfaces provide contact with angled sides of the spine rod holder opening. In another form, the spine rod has an essentially V-shaped cross-section that defines sides/side surfaces that interact with the spinal rod holder opening. Preferably, but not necessarily, the spine rod is formed of PEEK. Other bio-compatible materials, however, may be used.

13 Claims, 4 Drawing Sheets

(56) References Cited

U.S. PATENT DOCUMENTS

| | | | |
|---|---|---|---|
| 2011/0023612 A1* | 2/2011 | Ihara et al. | 73/632 |
| 2011/0238116 A1* | 9/2011 | Takemoto | 606/261 |
| 2012/0123480 A1* | 5/2012 | Freudiger | 606/278 |

* cited by examiner

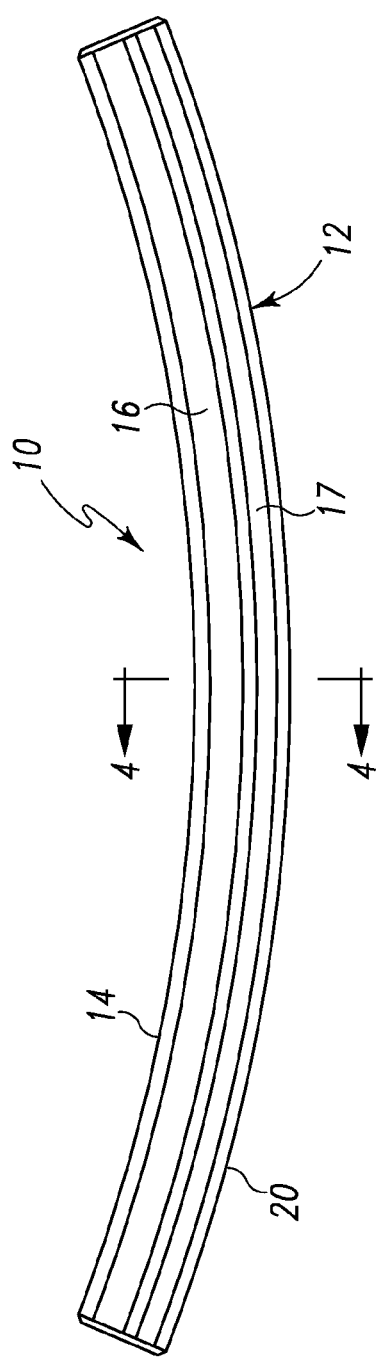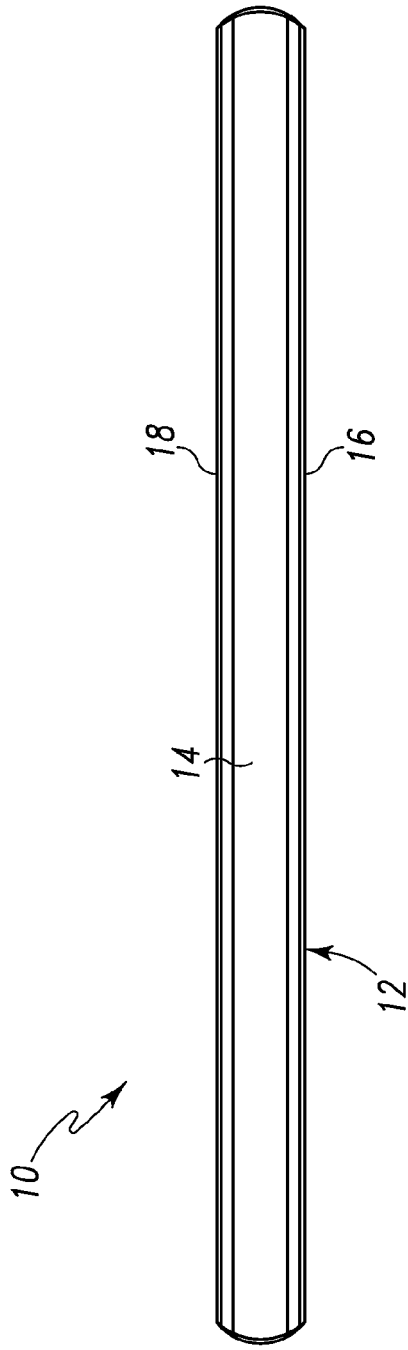

SPINAL ROD

RELATED APPLICATIONS

This patent application claims the benefit of and/or priority to U.S. Provisional Patent Application Ser. No. 61/095,650 filed Sep. 10, 2008, entitled "V-Shaped Spinal Rod" the entire contents of which is specifically incorporated herein by this reference.

BACKGROUND OF THE INVENTION

1. Field of the Invention

The present invention relates to devices for the stabilization of the spinal column and, more particularly, to spine or spinal rods used in the stabilization of the spinal column.

2. Background Information

A significant portion of the population suffers from spinal problems. Such spinal problems may be attributable to disease, trauma and/or other event. In the case of degenerative disc disease, spinal trauma and the like, such conditions are often painful and/or physically deforming. Depending on the situation, the pain and complications caused by these conditions may require that one or more vertebra, facet joints, and/or intervertebral discs be removed from the spinal column. In these procedures, bone fusion is a common treatment used to facilitate the realignment and/or fixation of the remaining spinal elements.

Currently, two types of systems or assemblies are utilized for securing and/or stabilizing one or more vertebrae in order to achieve bone fusion. One type of spine stabilizing assembly generally includes two posterior vertebral plates disposed longitudinally on either side of the spinous processes. Each plate is attached between adjacent vertebra using bone anchoring elements, such as bone screws. Together, the plates provide a rigid vertebral fixation.

Another type of spine stabilizing assembly generally includes two posterior vertebral rods disposed longitudinally on either side of the vertebrae (e.g. the spinous processes thereof). Like the plates, these rods are attached between adjacent vertebrae using appropriate bone anchoring devices to achieve rigid vertebral fixation.

These spine stabilizing assemblies are also used to correct spinal deformities such as scoliosis or the like. For this use, such spine stabilizing assemblies may have spine rods that span two or more vertebrae.

A drawback of current spinal rods relates to reception and seating of the spinal rod into the spinal rod holder/bone anchor assembly. Particularly, current spinal rods are round and must be securely retained in the spinal rod holder for proper spinal stabilization. The contact area between the round spinal rod and the U-shaped spinal rod holder is sparse given the two configurations. This low amount of contact area does not allow a good seating of the spinal rod into the rod holder. The spinal rod may be subject to loading that occurs on the stabilizing assemblies and especially on the anchoring sites during normal activity. These loads may result in loosening of the assembly from the vertebrae or even breaking of the assembly if there is not proper seating of the spinal rod in the spinal rod holder.

In view of the above, it is evident that there is thus a need for a spinal rod that provides the greatest extent of contact with a spinal rod holder.

In view of the above, it is further evident that there is thus a need for a spinal rod that is more securely received in a spinal rod holder than current spinal rods.

SUMMARY OF THE INVENTION

A spine implant, in the form of a spine or spinal rod, has a cross-section defining angled sides that cooperate with a spinal rod opening of a spinal rod holder to positively seat the spinal rod in the spinal rod holder.

In one form, the spine rod has an essentially pentagonal cross-section that thus essentially defines angled sides or side surfaces that interact with a configured spinal rod opening of a spine rod holder to positively seat the spine rod into the spinal rod holder. In this manner, the spine rod is prevented from rotational movement within the spinal rod holder.

In this form, the spine rod has a top or posterior side/side surface, a first lateral side/side surface, a second lateral side/side surface, a first angled sub-lateral side/side surface and a second angled sub-lateral side/side surface. A bottom or anterior side/side surface or point is defined at the junction of the first and second sub-lateral sides/side surfaces. The first and second angled sub-lateral sides/side surfaces provide contact with angled sides of the spine rod holder opening.

In one form, the spine rod has an essentially V-shaped cross-section defining first and second sides/side surfaces that provide contact with the angled sides of the spine rod holder opening.

The posterior surface is essentially flat or planar while the first and second lateral surfaces extend from the posterior surface and meet at the anterior surface. The first lateral surface has an angled portion at a lower end thereof that tapers to join at the bottom surface. The second lateral surface has an angled portion at a lower end thereof that tapers to join the bottom surface. The lower angled portions of the first and second lateral surfaces provide contact surfaces between the spinal rod and a spinal rod holder. The anterior surface forms the trough of the V-shaped cross section of the spine rod.

Preferably, but not necessarily, the present spinal rod is formed of PEEK, however, other bio-compatible materials may be used.

The present spine rod also preferably, but not necessarily, has a curvature, bend or angle that angles in the superior/inferior direction (when installed on the spinal column).

BRIEF DESCRIPTION OF THE DRAWINGS

The above mentioned and other features, advantages and objects of this invention, and the manner of attaining them, will become apparent and the invention itself will be better understood by reference to the following description of an embodiment of the invention taken in conjunction with the accompanying drawings, wherein:

FIG. 2 is a side view of the spinal rod of FIG. 1;

FIG. 3 is a top view of the spinal rod of FIG. 1;

Like reference numerals indicate the same or similar parts throughout the several figures.

An overview of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF AN EMBODIMENT OF THE INVENTION

Referring to FIGS. 1-4 there is depicted an exemplary embodiment of a spine implant formed as a spine or spinal rod generally designated 10 fashioned in accordance with the principles of the present invention. The spinal rod 10 is made from a biocompatible material such as PEEK, titanium or stainless steel, but is preferably made from PEEK. However, other biocompatible materials or compounds may be used such as a polymer, plastic, metal alloy, composite or the like. The spinal rod 10 has a cross-section defining angled sides that cooperate with a spinal rod opening of a spinal rod holder to positively seat the spinal rod in the spinal rod holder.

Figure 1:
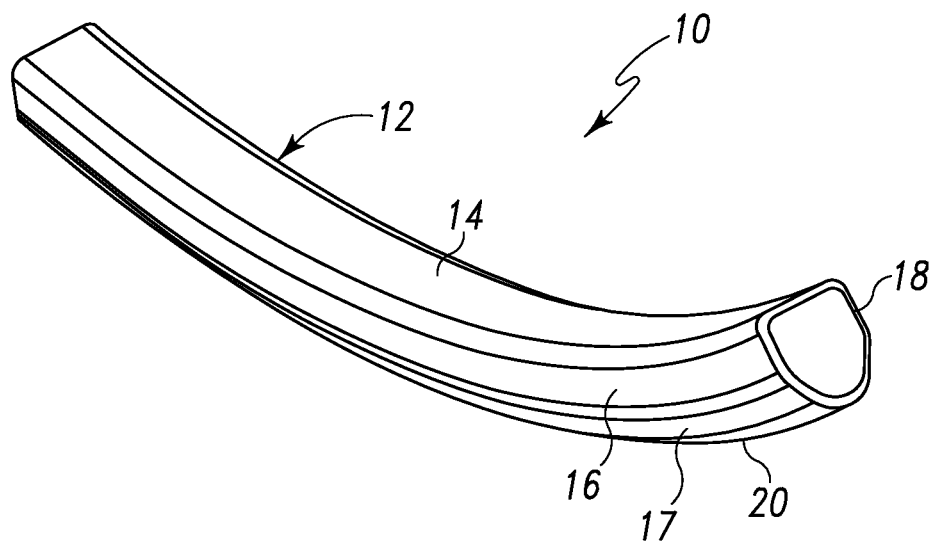
FIG. 1 is a perspective view of an exemplary spinal rod fashioned in accordance with the present principles.
Figure 4:
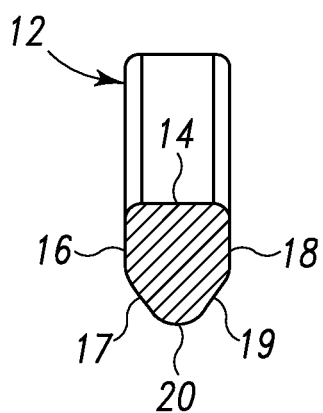
FIG. 4 is a sectional view of the spine rod of FIG. taken along line 4-4 of FIG. 2.
Figure 5:
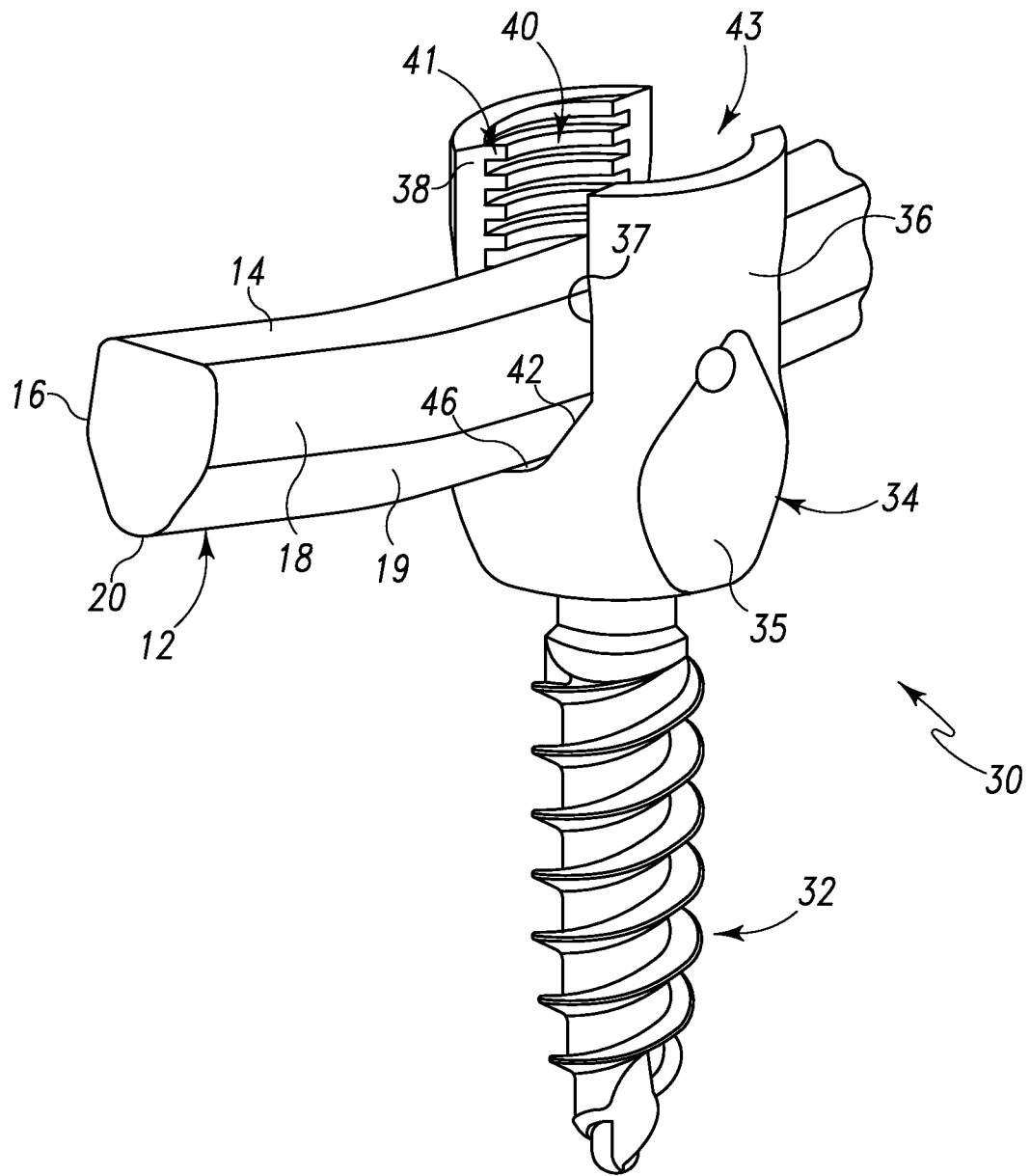
FIG. 5 is a perspective view of a spinal rod anchoring assembly in which is situated the spinal rod of FIG. 1.
Figure 6:
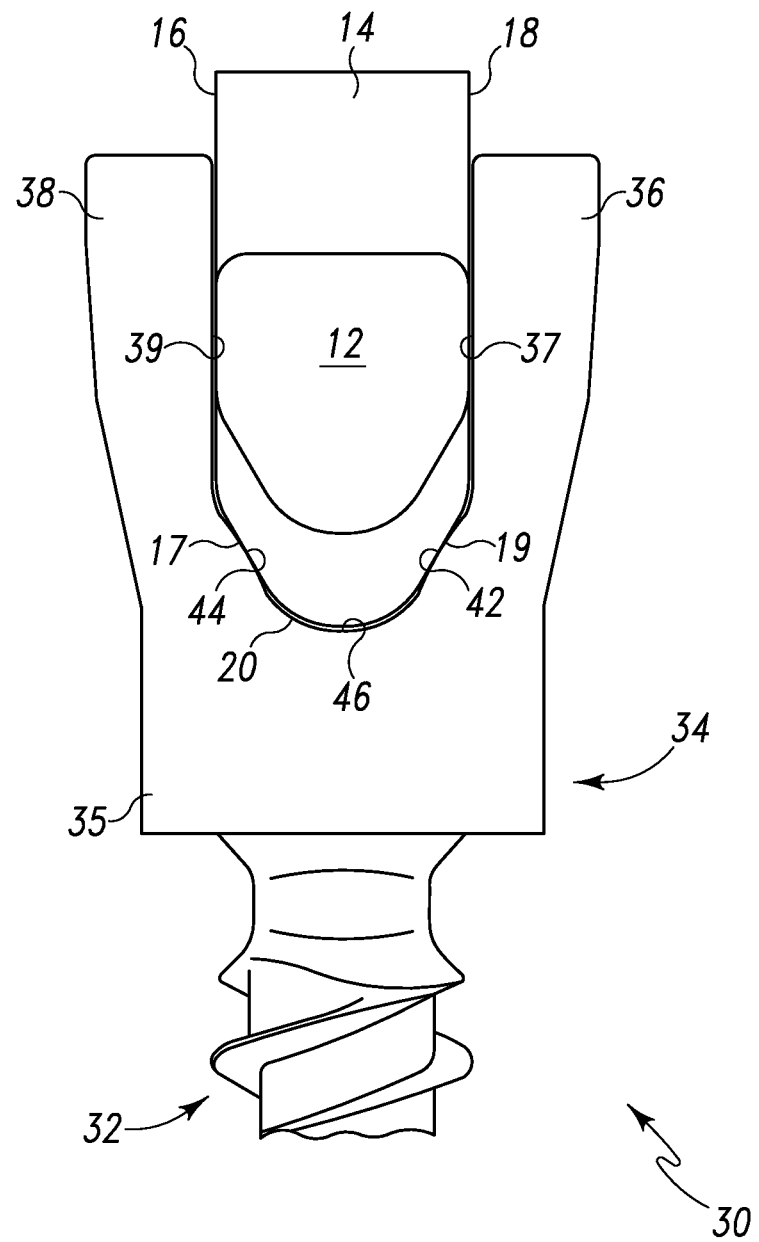
FIG. 6 is a side view of the spinal rod anchoring assembly and spinal rod of FIG. 5.

The spinal rod 10 is defined by a body 12 of a particular length. The body 12 has an essentially pentagonal or V-shaped cross-section such as is best seen in FIG. 4. The body 12 thus defines several sides or side surfaces. Particularly, the body 12 has a top or posterior side/side surface 14, a first lateral side/side surface 16, a second lateral side/side surface 18, a first sub-lateral side/side surface 17 and a second sub-lateral side/side surface 19. A bottom or anterior side/side surface 20 is defined at the junction or juncture of the first and second sub-lateral sides 17, 19. The anterior surface 20 is essentially a curved juncture of junction. Again, as best seen in FIG. 4, the posterior side 14 is essentially planar while the first and second lateral sides 16 and 18 extend generally perpendicular from the posterior side 14. The first sub-lateral side 17 extends from the first lateral side 16 and terminates at the anterior side 20. The second sub-lateral side 19 extends from the second lateral side 18 and terminates at the anterior side 20. The two sub-lateral sides 17, 19 taper or angle inwardly at lower ends thereof to join at the bottom 20. As seen in FIGS. 5 and 6 and discussed further below, the angled sub-lateral sides 17, 19 provide contact surfaces between the spinal rod 10 and a spinal rod holder (spinal rod holder opening) in order to securely and/or firmly seat the spinal rod 10 into the spinal rod holder. The anterior side 20 forms the trough of the V-shaped cross section of the body 12 or the fifth side of the pentagonal cross-section of the body 12.

As seen in the figures, the body 12 is shown having an arch, bend or curve that angles in the superior/inferior direction when installed (see e.g. FIGS. 5-6) on the spinal column. The amount of curvature may vary depending on the situation and thus the spinal rod 10 may be made not only in different lengths, but with different curvatures. The spinal rod 10 may also not have a curvature.

Referring specifically to FIGS. 5 and 6, the spinal rod 10 is shown received in a spinal rod holder/spinal rod attachment assembly 30 formed of a bone screw 32 and a spine rod holder or head 34. The bone screw 32 is retained by the spine rod holder 34 for polyaxial movement of the spine rod holder 34 relative to the bone screw 32. The spine rod holder 34 is a "tulip" head formed by a base 35 and first and second flanges or sides 36, 38, the first side having a threaded inside surface and the second side having a threaded inside surface. The spinal rod holder 34 defines an interior 40 while a first slot 41 is formed between one side of the first and second sides 36, 38 while a second slot 43 is formed between another side of the first and second sides 36, 38. The first and second slots 41, 43 are disposed diametrically opposite one another and form/provide a spinal rod opening. Additionally, the first and second slots are identical—so the description of one slot is applicable to the other slot. It should also be appreciated that the nomenclature first and second is arbitrary unless indicated otherwise.

As best seen in FIG. 6, the slot 41 is configured in an essentially V-shape that essentially corresponds to the shape of the spinal rod 10. The slot 41 is defined by a first lateral side 37, a second lateral side 39, a bottom 46, a first angled portion 42 connecting the first lateral side 37 to the bottom 46, and a second angled portion 44 connecting the second lateral side 39 to the bottom 36. It can be seen that these portions of the slot 41 correspond to the shape of the spinal rod 10 such that contact surfaces are defined therebetween. As indicated above, the slot 43 is identical.

The spinal rod 10 is thus received in the slots 41, 43 in a secure and snug manner. As seen in FIG. 6, the sub-lateral side 17 of the spine rod 10 meets and wedges against the angled portion 44 of the slot 41 while the sub-lateral side 19 of the spine rod 10 meets and wedges against the angled portion 42 of the slot 41. While not seen, the sub-lateral sides 17, 19 also meet and wedges against the like angled portions of the slot 43. Moreover, because of the mating configurations between the spinal rod 10 and the slots 41, 43, there is no tendency for the spine rod 10 to rotate once received in the spine rod holder 34. Additionally, the essentially flat or planar posterior or top surface 14 provides a good seat for a spine rod securing nut that is received by the spine rod holder 34 to retain the spine rod in the spine rod holder.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:
1. A spinal rod comprising:
an elongated body having a given length and a curvature along the given length such that the elongated body curves in a superior-inferior manner when implanted along a spine, the elongated body being formed of a biocompatible material;
the elongated body having a solid cross-section defined by a plurality of sidewalls, the plurality of sidewalls defining an outer periphery of the spinal rod and configured to engage a corresponding slot in a spinal rod holder, the plurality of sidewalls comprising:
a posterior sidewall;
a pair of lateral sidewalls extending from opposite ends of the posterior sidewall at substantially right angles and parallel to one another; and
a pair of planar sub-lateral sidewalls, each planar sub-lateral sidewall extending relative to one of the lateral sidewalls at an obtuse angle and relative to the other planar sub-lateral sidewall at an acute angle and toward a junction;
wherein the junction defines an anterior rounded intersection of the pair of planar sub-lateral sidewalls.
2. The spinal rod of claim 1, wherein the biocompatible material comprises PEEK.
3. The spinal rod of claim 1, wherein the pair of planar sub-lateral sidewalls provide contact points with angled sides of a spine rod holder opening.
4. The spinal rod of claim 3, wherein the pair of planar sub-lateral sidewalls join at the junction to form a curved anterior side.

5. A spinal rod comprising:
an elongated body of a given length and a curvature along the given length such that the elongated body curves in a superior-inferior manner when implanted along a spine, the elongated body being formed of a biocompatible material;
the elongated body having a solid cross-section defined by a plurality of sidewalls, the plurality of sidewalls defining an outer periphery of the spinal rod and configured to engage a corresponding slot in a spinal rod holder, the plurality of sidewalls comprising:
a first generally planar sidewall;
second and third sidewalls extending from opposite ends of the first sidewall and perpendicular to the first sidewall; and
planar fourth and fifth sidewalls extending relative to the second and third sidewalls at obtuse angles such that the planar fourth and fifth sidewalls extend relative to one another at an acute angle toward a curved junction opposite the first generally planar sidewall.

6. The spinal rod of claim 5, wherein the biocompatible material comprises PEEK.

7. The spinal rod of claim 5, wherein the planar fourth and fifth sidewalls provide contact points with angled sides of a spine rod holder opening.

8. The spinal rod of claim 7, wherein the planar fourth and fifth sidewalls join to form a curved anterior side.

9. A spinal implant for stabilizing vertebrae of a spine, the spinal implant comprising:
a body formed of an elongated rod of a biocompatible material, the body having a curvature along a length;
the body having a solid cross-sectional shape defining a plurality of sidewalls, the plurality of sidewalls including:
a posterior sidewall;
a first lateral sidewall extending from the posterior sidewall'
a second lateral sidewall extending from the posterior sidewall parallel to the first lateral sidewall;
a first planar sub-lateral sidewall extending relative to the first lateral sidewall at an obtuse angle; and
a second planar sub-lateral sidewall extending relative to the second lateral sidewall at an obtuse angle and relative to the first planar sub-lateral sidewall at an acute angle;
wherein the first and second planar sub-lateral sidewalls are configured to wedge against first and second angled sides of first and second respective slots of a spinal rod holder.

10. The spinal implant of claim 9, wherein the biocompatible material comprises PEEK.

11. The spinal implant of claim 9, wherein the curvature is in a superior/inferior direction.

12. The spinal implant of claim 9, wherein the cross-sectional shape is pentagonal.

13. The spinal implant of claim 9, wherein the cross-sectional shape is V-shaped.

* * * * *